United States Patent [19]

Re et al.

[11] 4,232,169

[45] Nov. 4, 1980

[54] PROCESS FOR PREPARING ALPHA-OXO-ESTERS

[75] Inventors: Luciano Re; Alberto Brandt, both of Rome; Luciano Bassignani, Passo Corese, all of Italy

[73] Assignee: Snamprogetti S.p.A., Milan, Italy

[21] Appl. No.: 33,014

[22] Filed: Apr. 24, 1979

Related U.S. Application Data

[63] Continuation of Ser. No. 831,237, Sep. 7, 1977, abandoned.

[30] Foreign Application Priority Data

Oct. 6, 1976 [IT] Italy .................................. 28041 A/76

[51] Int. Cl.² ...................... C07C 67/00; C07C 69/67; C07C 69/95
[52] U.S. Cl. .................................. 560/174; 260/410; 260/410.5; 260/410.9 R; 423/22; 560/51; 560/122; 560/123; 560/124; 560/126

[58] Field of Search .................. 560/174, 126, 51, 122, 560/123, 124; 260/410, 410.5, 410.9 R; 423/22

[56] References Cited

U.S. PATENT DOCUMENTS 3,048,622   8/1962   Stansbury et al. ................... 560/174
3,065,259  11/1962   Kollonitsch .......................... 560/174

Primary Examiner—Vivian Garner
Attorney, Agent, or Firm—Morgan, Finnegan, Pine, Foley & Lee

[57] ABSTRACT

An operationally simple and economical process for preparing alpha-oxoesters is provided by reacting an acetylenic compound of formula

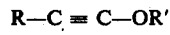

with an oxidizing mixture composed of osmium tetroxide and an alkaline or alkaline earth chlorate and recovering the osmium tetroxide at the end of the reaction.

10 Claims, No Drawings

PROCESS FOR PREPARING ALPHA-OXO-ESTERS

This is a continuation of application Ser. No. 831,237 filed Sept. 7, 1977, abandoned.

This invention relates to a process for preparing alpha-oxoesters of formula I

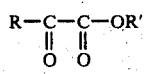    I in which R and R', the same or different, may be alkyl, aryl, arylalkyl or cycloalkyl groups, and in addition R may be hydrogen.

Alpha-oxoesters according to the present invention may be converted very easily into the corresponding alpha-oxoacids by methods known to any expert of the art.

Both alpha-oxoesters and alpha-oxoacids are useful synthesis intermediates particularly in the preparation of alpha-aminoesters or alpha-aminoacids, respectively by reductive amination or by reaction with hydroxylamine followed by catalytic hydrogenation.

More recently, asymmetric syntheses have been developed for obtaining optically active alpha-aminoacids from alpha-ketoacids (see for example E. J. Corey et al., J. Am. Chem. Soc., 92, 2476 (1970); K. Morada et al., Bull. Chem. Soc. Jap., 43, 921-1970).

In the process according to the present invention, alpha-oxoesters are prepared from acetylenic derivatives of general formula II:

    II in which R and R' have the same meanings as heretofore, by reaction with an oxidizing mixture composed of osmium tetroxide and an alkaline or alkaline earth chlorate.

Relative to known methods for preparing the aforesaid alpha-oxoesters, the method according to the present invention has the advantage of being not only operationally more simple, but also more economical in that the osmium tetroxide may be recovered at the end of the reaction.

Furthermore, the crude product obtained has in many cases a degree of purity sufficient to allow it to be used as such in the next process stage.

In the process according to the present invention, the oxidizing agent for the acetylenic compound is osmium tetroxide, the chlorate serving to regenerate the osmium tetroxide in situ, so that this latter may be used in catalytic quantites.

As stated, the osmium tetroxide may be recovered at the end of the reaction, either by entraining it in a stream of nitrogen and collecting it in a no longer volatile form in a trap containing the initial acetylenic compound of a subsequent batch, or by precipitating it with sulphidric acid in the form of osmium sulphide, which may be recycled as such, as the chlorate reoxidizes it to osmium tetroxide, or by any other methods known to any expert of the art.

The initial acetylenic derivatives of type II may be notably prepared from aldehydes of formula $RCH_2CHO$ in which R has the same meaning as heretofore, or from other commercial products following known procedures such as described for example in J. F. Arens, Adv Org. Chem., 2,121, (1960), or in L. Bradsma, H. J. T. Bos, J. F. Arens "Acetylenic Ethers and Thioethers" in "Chemistry of Acetylenes" H. C. Viehe, Ed., Marcel Dekker inc., New York, 1969, p. 750.

The acetylenic compound oxidation reaction is carried out in water or a monophase or bi-phase mixture of water with an inert organic solvent (preferably ethyl ether) at a temperature of 0°–100° C. (generally at ambient temperature) and at a pressure such as to maintain the liquid phase in the system.

In some cases it is advantageous to work at a controlled pH (5.5–7.5) which may be attained in various ways, for example by means of an automatic titrator.

The operational details will be more evident from the illustrative examples given hereinafter, which however in no way limit the invention.

EXAMPLE 1

Preparation of methyl pyruvate from 1-propinyl methylether 12.7 g (0.181 moles) of 1-propinyl methylether are added at ambient temperature over a period of 20 minutes to an agitated mixture of 200 ml of water, 300 ml of ethylether, 36 g (0.294 moles) of potassium chlorate and 2 g (0.0079 moles) of osmium tetroxide while maintaining the pH at 6.8 by means of an automatic titrator charged with 1 N KOH.

After a further 4 hours of agitation under the same condition, the black colouration of the mixture disappears and the ether phase is separated from the aqueous phase, and this latter is extracted with ethylether in a liquid-liquid extractor.

Sulphydric acid is dripped slowly for 10 min. at 0° C. into the combined ether solutions made anhydrous ($Na_2SO_4$), the formed precipitate is digested for a further 15 min. at 0° C., and the osmium sulphide is then filtered, and may be re-used as such, as it is re-oxidized to osmium tetroxide by the chlorate.

The ether solution is concentrated at 0° C. in the rotating evaporator and the residue is distilled (Vigreux column) under a vacuum of 15 mmHg collecting the fraction with a B.P. of 50°–53° C. (boiler 85° C.).

8.65 g (0.085 moles) of gas-chromatographically pure product are obtained. Yield: 46.8%. B.P. 134° C.; ir (film): $\nu$max 1725 cm$^{-1}$ (CO of ester and ketone); NMR ($C_6D_6$): delta 2.45 (3H, s, $CH_3CO$); 3.75 (3H, s, $COOCH_3$).

EXAMPLE 2

Preparation of methyl alpha-ketobutyrate from 1-butinyl methylether

A mixture of 120 ml of water, 210 ml of ethyl ether, 16.7 g (0.136 moles) of potassium chlorate, 0.69 g (0.0027 moles of osmium tetroxide and 5.5 g (0.065 moles) of 1-butinyl methylether is agitated at ambient temperature for 16 hours.

After processing as described in example 1, distilling the crude under a vacuum of 27 mmHg and collecting the fraction with a B.P. of 72°–74° C. (boiler 100°–105° C.), 5.2 g (0.045 moles of gas-chromatographically pure methyl alpha-ketobutyrate are obtained. Yield: 69%. Ir (film): $\nu$max 1730 cm$^{-1}$ (CO of ester and ketone); NMR ($C_6D_6$): delta 0.90 (3H, t, J=6 Hz, $CH_3C$), 2.57 (2H, q, J=6 Hz, $CH_2CO$), 3.53 (3H, s, $COOCH_3$).

EXAMPLE 3

Preparation of methyl alpha-ketoisovaleriate from isopentinyl methylether.

A mixture of 200 ml of water, 350 ml of ethyl ether, 40.2 g (0.328 moles) of potassium chlorate, 1.66 g (0.0065 moles) of osmium tetroxide and 14.6 g (0.149 moles) of isopentinyl methylether is agitated at ambient temperature for 16 hours.

After processing as described in example 1, distilling the crude under a vacuum of 23 mmHg and collecting the fraction with B.P. of 64°–68° C., 15.5 g (0.119 moles) of gas-chromatographically pure methyl alpha-ketoisovaleriate are obtained. Yield: 79.9%. Ir (film): $\nu$max 1730 cm$^{-1}$ (CO of ester and ketone); NMR (C$_6$D$_6$): delta 1.08 (6H, d, J=6 Hz, (CH$_3$)$_2$C), 3.15 (1H, m, J=6 Hz, CH), 3.42 (3Hn s, COOCH$_3$).

What we claim is:

1. A process for preparing alpha-oxoesters corresponding to the general formula $$R-\underset{\underset{O}{\|}}{C}-\underset{\underset{O}{\|}}{C}-OR^1$$

in which R and R$^1$, the same or different, may be alkyl, aryl, arylalkyl or cycloalkyl groups, and in addition R may be hydrogen, consisting of reacting an acetylenic compound of the formula $$R-C\equiv C-OR'$$

wherein R and R$^1$ are the same as hereinabove defined, with a mixture of osmium tetroxide and an alkali metal or alkaline earth metal chlorate in the liquid phase at a temperature of about 0° C. to about 100° C. and thereafter recovering the product.

2. A process for preparing alpha-oxoesters as claimed in claim 1 wherein the osmium tetroxide is recovered by entraining the osmium tetroxide in a stream of nitrogen and collecting the osmium tetroxide in a liquid form in a trap containing an acetylenic compound of the formula R—C≡COR' wherein R and R$^1$ are the same as hereinabove defined.

3. A process for preparing alpha-oxoesters as claimed in claim 1 wherein the osmium tetroxide is recovered as osmium sulphide by precipitation with hydrogen sulfide.

4. A process for preparing alpha-oxoesters as claimed in claim 1, wherein the oxidation of the acetylenic compound is carried out in water or in a monophase or bi-phase mixture of water with an inert organic solvent.

5. A process for preparing alpha-oxoesters as claimed in claim 4, wherein the oxidation of the acetylenic compound is carried out in the presence of a mixture of water and an inert organic solvent wherein said inert organic solvent is ethyl ether.

6. A process for preparing alpha-oxoesters as claimed in claim 4, wherein the oxidation of the acetylenic compound is carried out at ambient temperature.

7. A process for preparing alpha-oxoesters of the formula $$R-\underset{\underset{O}{\|}}{C}-\underset{\underset{O}{\|}}{C}-OR^1$$

in which R and R$^1$ are the same or different and are selected from alkyl, aryl, arylalkyl or cycloalkyl groups and in addition R may be hydrogen, said process comprising oxidizing an acetylenic compound of the formula R—C≡COR' wherein R and R$^1$ are the same as hereinabove defined, with a mixture of osmium tetroxide and an alkali metal or alkaline earth metal chlorate in the liquid phase at a temperature of 0°–100° C. and a pH of 5.5 to 7.5.

8. A process as defined in claim 7 wherein the acetylenic compound is 1-propinyl methylether and the alkali metal chlorate is potassium chlorate.

9. A process as defined in claim 7 wherein the acetylenic compound is 1-butinyl methylether and the alkali metal chlorate is potassium chlorate.

10. A process as defined in claim 7 wherein the acetylenic compound is isopentinyl methylether and the alkali metal chlorate is potassium chlorate.

* * * * *